(12) United States Patent
Cao et al.

(10) Patent No.: US 11,957,409 B2
(45) Date of Patent: Apr. 16, 2024

(54) IRRIGATION COOLING STRUCTURE FOR MICROWAVE ABLATION TISSUE PROBE

(71) Applicant: Boston Scientific Scimed, Inc., Maple Grove, MN (US)

(72) Inventors: Hong Cao, Maple Grove, MN (US); Timothy A. Ostroot, Cokato, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 501 days.

(21) Appl. No.: 16/717,113

(22) Filed: Dec. 17, 2019

(65) Prior Publication Data

US 2020/0197089 A1  Jun. 25, 2020

Related U.S. Application Data

(60) Provisional application No. 62/782,149, filed on Dec. 19, 2018.

(51) Int. Cl.
*A61B 18/00* (2006.01)
*A61B 18/18* (2006.01)

(52) U.S. Cl.
CPC ............... *A61B 18/1815* (2013.01); *A61B 2018/00035* (2013.01); *A61B 2018/00577* (2013.01); *A61B 2018/183* (2013.01); *A61B 2018/1869* (2013.01)

(58) Field of Classification Search
CPC .......... A61B 2018/00005; A61B 2018/00011; A61B 2018/00017; A61B 2018/00023; A61B 2018/00035; A61B 18/1815; A61B 2018/00577; A61B 2018/183; A61B 2018/1869; A61B 2018/1838
See application file for complete search history.

(56) References Cited

U.S. PATENT DOCUMENTS

| 4,823,812 A | 4/1989 | Eshel et al. |
| 5,348,554 A | 9/1994 | Imran et al. |

(Continued)

FOREIGN PATENT DOCUMENTS

| CN | 113194860 | 7/2021 |
| WO | 2020132058 | 6/2020 |

OTHER PUBLICATIONS

Wettability_effects_on_heat_transfer_proof_of_date (Year: 2023).*

(Continued)

*Primary Examiner* — Michael F Peffley
*Assistant Examiner* — Nicholas S Borsch
(74) *Attorney, Agent, or Firm* — Pauly, DeVries Smith Deffner LLC (57) ABSTRACT

A microwave ablation probe including a probe body including a shielded portion and a radiation window that is at least partially transparent to microwave energy. The shielded portion includes a cannula, a coaxial cable within the probe body, and an antenna comprising a radiating portion for emission of microwave energy at a distal portion of the probe body, wherein the radiating portion is aligned with the radiation window. The probe body defines an irrigation path configured to carry cooling fluid to and from the distal portion of the probe body. At least one wall defining the irrigation path comprises a heat exchange surface having an average radius, wherein a surface area of the heat exchange surface is larger than a surface area of a smooth surface with a radius equal to the average radius.

20 Claims, 6 Drawing Sheets

(56) References Cited

U.S. PATENT DOCUMENTS

| | | | |
|---|---|---|---|
| 5,807,395 A | 9/1998 | Mulier et al. | |
| 5,810,804 A | 9/1998 | Gough et al. | |
| 6,030,379 A | 2/2000 | Panescu et al. | |
| 6,241,722 B1* | 6/2001 | Dobak | A61B 18/02 606/23 |
| 6,379,378 B1* | 4/2002 | Werneth | A61F 7/12 607/105 |
| 6,514,251 B1 | 2/2003 | Ni et al. | |
| 8,235,981 B2* | 8/2012 | Prakash | A61B 18/18 606/41 |
| 8,279,604 B2 | 10/2012 | Jones et al. | |
| 9,579,150 B2* | 2/2017 | DeCarlo | A61B 18/1815 |
| 9,820,814 B2 | 11/2017 | Turovskiy et al. | |
| 11,382,682 B2 | 7/2022 | Ostroot et al. | |
| 2002/0026188 A1 | 2/2002 | Balbierz et al. | |
| 2004/0116921 A1 | 6/2004 | Sherman et al. | |
| 2004/0176761 A1 | 9/2004 | Desinger | |
| 2004/0220562 A1 | 11/2004 | Garabedian et al. | |
| 2006/0122593 A1 | 6/2006 | Jun | |
| 2006/0178666 A1 | 8/2006 | Cosman et al. | |
| 2008/0147060 A1 | 6/2008 | Choi | |
| 2009/0295674 A1* | 12/2009 | Bonn | A61B 18/18 343/872 |
| 2011/0066144 A1* | 3/2011 | Bonn | A61B 18/1815 29/600 |
| 2011/0264084 A1* | 10/2011 | Reid | A61B 18/02 606/23 |
| 2013/0281851 A1 | 10/2013 | Carr | |
| 2015/0272669 A1 | 10/2015 | Brucker et al. | |
| 2016/0095657 A1 | 4/2016 | Brannan | |
| 2019/0015152 A1* | 1/2019 | Howard | A61B 18/1492 |
| 2020/0163709 A1 | 5/2020 | Ostroot et al. | |
| 2022/0296292 A1 | 9/2022 | Ostroot et al. | |

OTHER PUBLICATIONS

Chiwoong Choi et al, Wettability Effects on Heat Transfer, 2011 (Year: 2011).*

"International Search Report and Written Opinion," for PCT Application No. PCT/US2019/067155 dated Mar. 13, 2020 (13 pages).

"International Preliminary Report on Patentability," for PCT Application No. PCT/US2019/067155 dated Jul. 1, 2021 (8 pages).

"Response to Communication Pursuant to Rules 161(1) and 162 EPC," for European Patent Application No. 19839060.1 filed Aug. 10, 2021 (10 pages).

"Notice of Allowance," for U.S. Appl. No. 16/695,622 dated Mar. 7, 2022 (19 pages).

"Non-Final Office Action," for U.S. Appl. No. 17/838,012 mailed Jan. 19, 2024 (16 pages).

* cited by examiner

IRRIGATION COOLING STRUCTURE FOR MICROWAVE ABLATION TISSUE PROBE

This application claims the benefit of U.S. Provisional Application No. 62/782,149 filed Dec. 19, 2018, the content of which is herein incorporated by reference in its entirety.

BACKGROUND

Microwave ablation (MWA) is a minimally invasive energy modality for body treatments in many locations, including soft tissue lesions in the liver, kidney and lung. Microwave ablation probes use an antenna, such as a monopole or dipole antenna, to radiate microwave energy into tissue for heating. Unlike radiofrequency ablation, which depends on ion movement and friction for heating, microwave ablation energy causes water molecules to rotate due to the polarity of the molecules and generates heat due to hysteresis. It typically operates at industrial, scientific and medical (ISM) radio bands such as 500 MHz to 10 GHz, and more specifically can operate at 945 MHz or 2.45 GHz. Microwave ablation has advantages such as fast heating, allowing the probe to operate at high temperature to create larger lesions, and has been gaining market share over the past decade over radiofrequency ablation (RFA) for tissue ablation.

SUMMARY

One general aspect includes a microwave ablation probe including: a probe body including a shielded portion and a radiation window that is at least partially transparent to microwave energy, where the shielded portion includes a cannula. The microwave ablation probe also includes a coaxial cable within the probe body. The microwave ablation probe also includes an antenna including a radiating portion for emission of microwave energy at a distal portion of the probe body, where the radiating portion is aligned with the radiation window. The probe body defines an irrigation path configured to carry cooling fluid to and from the distal portion of the probe body, where at least one wall defining the irrigation path includes a heat exchange surface. The heat exchange surface has an average radius, where a surface area of the heat exchange surface is larger than a surface area of a smooth surface with a radius equal to the average radius.

Implementations may include one or more of the following features. The heat exchange surface includes corrugations, undulations, fins, one or more ridges, an axial corrugation, a helical corrugation, a radial corrugation, a helical ridge, a radial ridge, or an axial ridge. The heat exchange surface varies in distance from a longitudinal axis of the probe. The heat exchange surface is located on at least a portion of an outer surface of an outer conductor of the cable. The heat exchange surface is located on at least a portion of an inner surface of the cannula. The heat exchange surface includes a helical ridge on at least a portion of an outer surface of an outer conductor of the cable. The heat exchange surface includes a helical ridge on at least a portion of an inner surface of the cannula. The heat exchange surface includes a helical ridge on at least a portion of an outer surface of an outer conductor of the cable, where the probe further includes an additional heat exchange surface, the additional heat exchange surface including a helical ridge on at least a portion of an inner surface of the cannula. The heat exchange surface includes axial corrugations on at least a portion of an inner surface of the cannula. The heat exchange surface includes axial corrugations on at least a portion of an outer surface of an outer conductor of the cable. The heat exchange surface includes axial corrugations on at least a portion of an inner surface of the cannula, where the probe further includes an additional heat exchange surface, the additional heat exchange surface including axial corrugations on at least a portion of an outer surface of an outer conductor of the cable. The probe may further include a coolant source configured to deliver the cooling fluid to the irrigation path and receive the cooling fluid. The probe may further include a liner concentric with and within the cannula, where a first segment of the irrigation path is defined between an outer surface of an outer conductor and an inner surface of liner, where a second segment of the irrigation path is defined between an outer surface of the liner and an inner surface of the cannula. The first segment of the irrigation path is an inlet path and the second segment of the irrigation path is an outlet path. The cannula includes a cannula wall that defines at least one lumen for a flow of cooling fluid.

One general aspect includes a microwave ablation system including a microwave energy source, a cooling fluid source, and a microwave ablation probe, the probe including: a probe body including a shielded portion and a radiation window that is at least partially transparent to microwave energy, where the shielded portion includes a cannula. The microwave ablation system also includes a coaxial cable within the probe body connected to the microwave energy source, the cable including a center conductor, a dielectric material surrounding the center conductor, and an outer conductor having an outer surface and a distal boundary, where the center conductor includes a radiating portion that extends beyond the distal boundary of the outer conductor, where the radiating portion is configured for emission of microwave energy, where the radiating portion is aligned with the radiation window. The microwave ablation system also includes where the probe body defines an irrigation path configured to carry cooling fluid to and from a distal portion of the probe body, where the cooling fluid source is in fluid communication with the irrigation path. The microwave ablation system also includes where at least one wall defining the irrigation path includes a heat exchange surface. The microwave ablation system also includes where the heat exchange surface has an average radius, where a surface area of the heat exchange surface is larger than a surface area of a smooth surface with a radius equal to the average radius.

Implementations may include one or more of the following features. The probe further including a liner concentric with and within the cannula, where a first segment of the irrigation path is defined between the outer surface of the outer conductor and an inner surface of liner, where a second segment of the irrigation path is defined between an outer surface of the liner and an inner surface of the cannula. The probe where the first segment of the irrigation path is an inlet path and the second segment of the irrigation path is an outlet path.

One general aspect includes a microwave ablation method including providing a microwave ablation probe including a probe body including a shielded portion and a radiation window that is at least partially transparent to microwave energy, where the shielded portion includes a cannula. The microwave ablation probe also includes a coaxial cable within the probe body. The microwave ablation probe also includes an antenna electrically connected with the cable and within the probe body, the antenna having a radiating portion for emission of microwave energy at a distal portion of the probe body. The microwave ablation method also includes where the radiating portion is aligned with the radiation window, where the probe body defines an irrigation path configured to carry cooling fluid to and from the distal portion of the probe body, where at least one wall defining the irrigation path includes a heat exchange surface, where the heat exchange surface has an average radius, and where a surface area of the heat exchange surface is larger than a surface area of a smooth surface with a radius equal to the average radius. The microwave ablation method also includes delivering cooling fluid to the irrigation path. The microwave ablation method also includes delivering microwave energy to the antenna via the cable.

Implementations may include one or more of the following features. The method further includes receiving cooling fluid back from the irrigation path at a cooling fluid source. Implementations of the described techniques may include hardware, a method or process, or computer software on a computer-accessible medium.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

Some of the figures are schematic in nature and are not drawn to scale. Certain features are shown larger than their scale and certain features are omitted from some views for ease of illustration. While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Various examples of the technology described herein provide an irrigated cooled microwave ablation probe and system. In one or more examples, the microwave ablation probe uses a coaxial cable antenna with a radiating portion to deliver microwave energy to tissue. The microwave energy heats the tissue, thus ablating the tissue. Energy is transmitted from an external microwave energy source through the proximal portion of the microwave ablation probe to the distal end of the microwave ablation probe, where it is transmitted into the patient tissue. Heating along the proximal portion of the microwave ablation probe can cause the ablated lesion to have an elongated tail or comet shape along the outside of the probe body. The design features of the disclosed technology can reduce the comet shape of the ablation lesion by including internal liquid cooling in the shaft of the microwave ablation probe. The irrigation can carry heat away from both the antenna and the probe shaft to reduce the temperature rise of both the antenna and the patient tissue. In some examples, a fin structure within the ablation probe is provided to improve the heat exchange between the cooling liquid and the internal components of the ablation probe. This can produce more spherical lesions.

In some examples of the disclosed technology, the ablation probe includes a microwave dipole antenna, which uses a coaxial cable to transmit microwave energy. A coolant enters the probe body through an inner lumen that is in contact with the coaxial antenna. The coolant exits the probe body through an exterior lumen to carry heat away from the outer cannula, which is in contact with patient tissue.

Without being bound by theory, the basic relationship for heat transfer by convection of a coolant through physical contact with a convective surface is described by the relationship $Q=hA(T_o-T_c)$, where Q is the heat transferred per unit time, A is the surface area of the convective surface that is contacted by the coolant, h is a heat transfer coefficient, $T_o$ is the convective surface's surface temperature, and $T_c$ is the temperature of the coolant.

The heat transfer coefficient h is dependent on the flow rate and other factors. An increased flow rate can increase the amount of heat carried away. However, a higher flow rate increases the pressures within the microwave ablation probe, which also increases mechanical strain on the small structures of the microwave ablation probe.

Various examples of the disclosed technology provide a heat exchange surface having surface features that create a surface area A that is greater than a surface area of a smooth surface. Some examples of the disclosed technology include surface features that cause a cooling fluid to follow a nonlinear path through the body of the ablation probe. Each of these examples increases the surface area A contacted by the cooling fluid. Because A is directly proportional to Q, the heat transferred from the ablation probe to the cooling fluid per unit time is increased. Because Q is the amount of heat transferred per unit time, the more time the coolant stays in contact with the convective surface, the more heat can be removed from the system.

As will be discussed later with regard to the figures, some examples of the disclosed technology provide an augmented heat exchange surface on an inner surface of the probe cannula. Some examples provide an augmented heat exchange surface on the outer surface of the coaxial cable antenna. Some examples provide augmented heat exchange surfaces on both the inner surface of the probe cannula and the outer surface of the coaxial cable antenna.

As used herein, the words proximal and distal express a relationship between two different elements. An element that is designated as being proximal is positioned closer to the external portion of the system, i.e., a portion that does not enter a patient's body. An element that is designated as being distal is positioned closer to the insertion end of the system.

Microwave Ablation System

Figure 1:
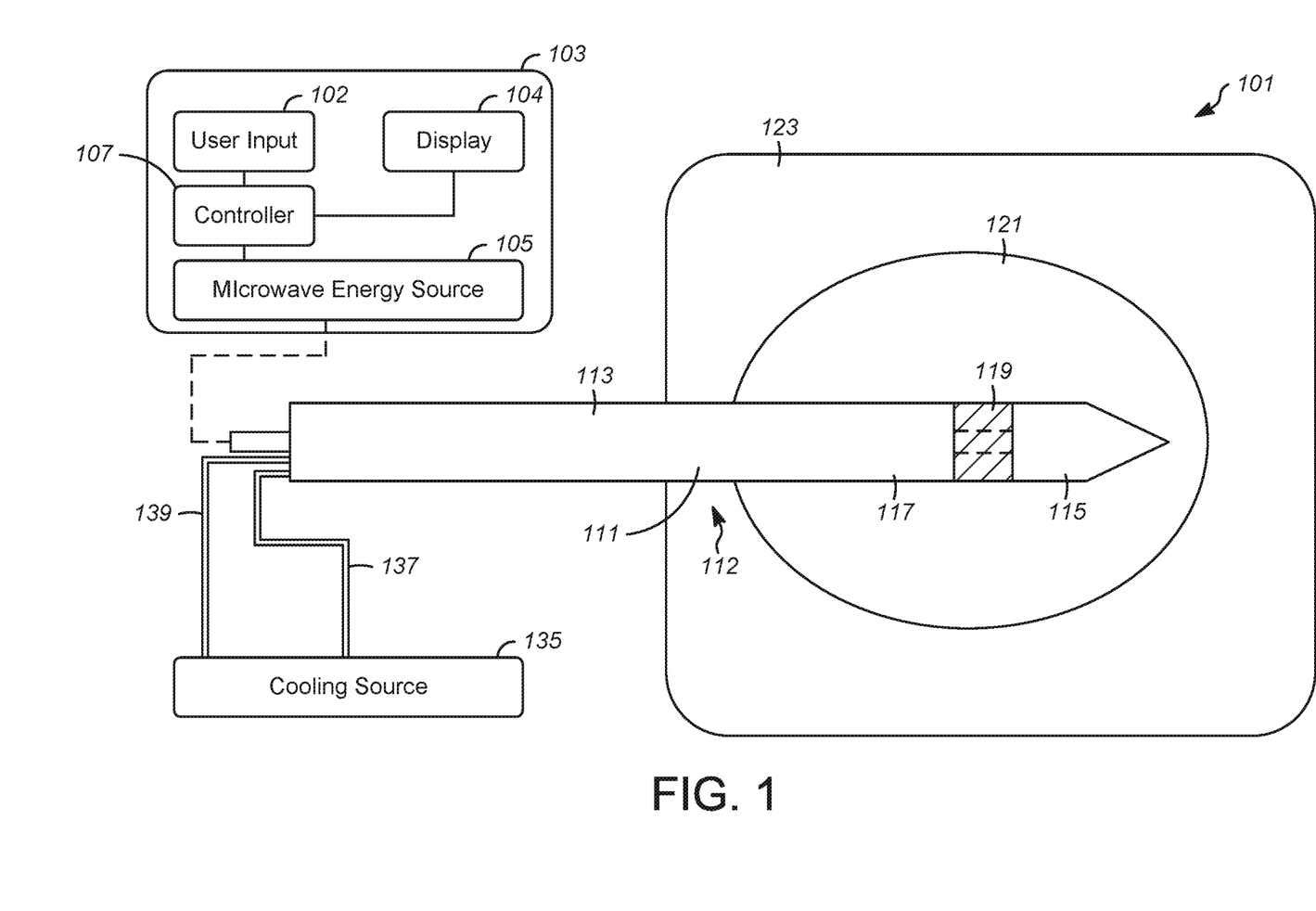
FIG. 1 is a schematic view of a microwave ablation system according to some examples.

Referring now to the figures, FIG. 1 is a schematic view of a microwave ablation system according to some examples. The system 101 includes a microwave ablation control unit 103, which includes a microwave energy source 105 that delivers microwave energy to an ablation probe 111. The microwave ablation control unit 103 also includes a controller 107, which can be a microprocessor that controls the microwave energy source, a user input 102, and a display 104, allowing a physician or other medical professional to monitor and interact with the control unit 103.

An available microwave ablation generator is the Sairem GMS solid state generator, operating at maximum of 200 W and 2450 MHz, manufactured by Sairem, of Neyron, France. Alternatively, the Emblation Microwave MSYS245 Medical System, operating at maximum of 100 W and 2450 MHz, manufactured by Emblation Microwave, an Emblation Limited Company, of Scotland, UK can be used. These commercial systems and any combination can be used to implement the system described herein.

Microwave Ablation Probe

The microwave ablation probe 111 includes a probe body 112 with a cannula 113 and a radiation window 119 at an insertion end 115 of the ablation probe 111. The radiation window 119 includes a length of an inner conductor 242 of a coaxial cable 251 that extends away from the end of an outer conductor 242 of the coaxial cable 251. The elongate probe body 112 can be provided in a variety of lengths. The length of the probe body 112 is much larger than its diameter. For example, the length may be 10 times the diameter or more, 50 times the diameter or more, 100 times the diameter or more, or 200 times the diameter or more. The length may be at least 5 centimeters or at least 10 centimeters. In some examples, the outer diameter of the probe body 112 is at least about 18 gauge (1.02 millimeters), at least about 17 gauge (1.15 millimeters), or at least about 16 gauge (1.29 millimeters). In some examples, the outer diameter of the probe body 112 is at most about 12 gauge (2.01 millimeters), at most about 13 gauge (1.83 millimeters), or at most about 14 gauge (1.63 millimeters).

The insertion end 115 is configured to be inserted into patient tissue 123. In some examples, the insertion end 115 has a tissue-piercing tip configured for percutaneous entry into patient tissue 123. The ablation probe 111 has a shielded portion 117 that prevents microwave energy from entering patient tissue along the cannula 113, and a radiation window 119 that is transparent to microwave energy, allowing microwave energy to be transmitted into the patient tissue 123, to create the lesion 121. The outer conductor 242 shields the patient's body from microwave along the shielded portion 117 of the ablation probe 111. The radiation window 119 includes material surrounding the central conductor 242 that is at least partially transparent to electromagnetic radiation emitted in the microwave range of the electromagnetic spectrum with a frequency on the order of about 300 megahertz to 300 gigahertz. Material examples for the radiation window 119 include fluoropolymers, urethanes, polyether block amides (PEBA), polypropylene, polyethylene, polyamide (nylon), polyimide, polyetherimide (PEI), polysulfone, and polyetheretherketone (PEEK). The length of the radiation window 119 is based on the particular antenna 252 used in the microwave ablation probe 111. In some examples, the length of the radiation window 119 is at least about 7 millimeters, at least about 10 millimeters, or at least about 13 millimeters. In some examples, the length is at most about 30 millimeters, or at most about 20 millimeters. In one example, the length is about 15 millimeters.

A cooling fluid reservoir 135 is connected to the ablation probe 111 to deliver cooling fluid into the system through a first conduit 137 and to receive circulated fluid out of the system through a second conduit 139. In some examples, the cooling fluid is a saline solution, such as a 0.9 percent saline solution. In alternative examples, the cooling fluid is deionized water. It is also possible to use other cooling fluids, and these equivalents fall within the scope of the disclosed technology.

Figure 2:
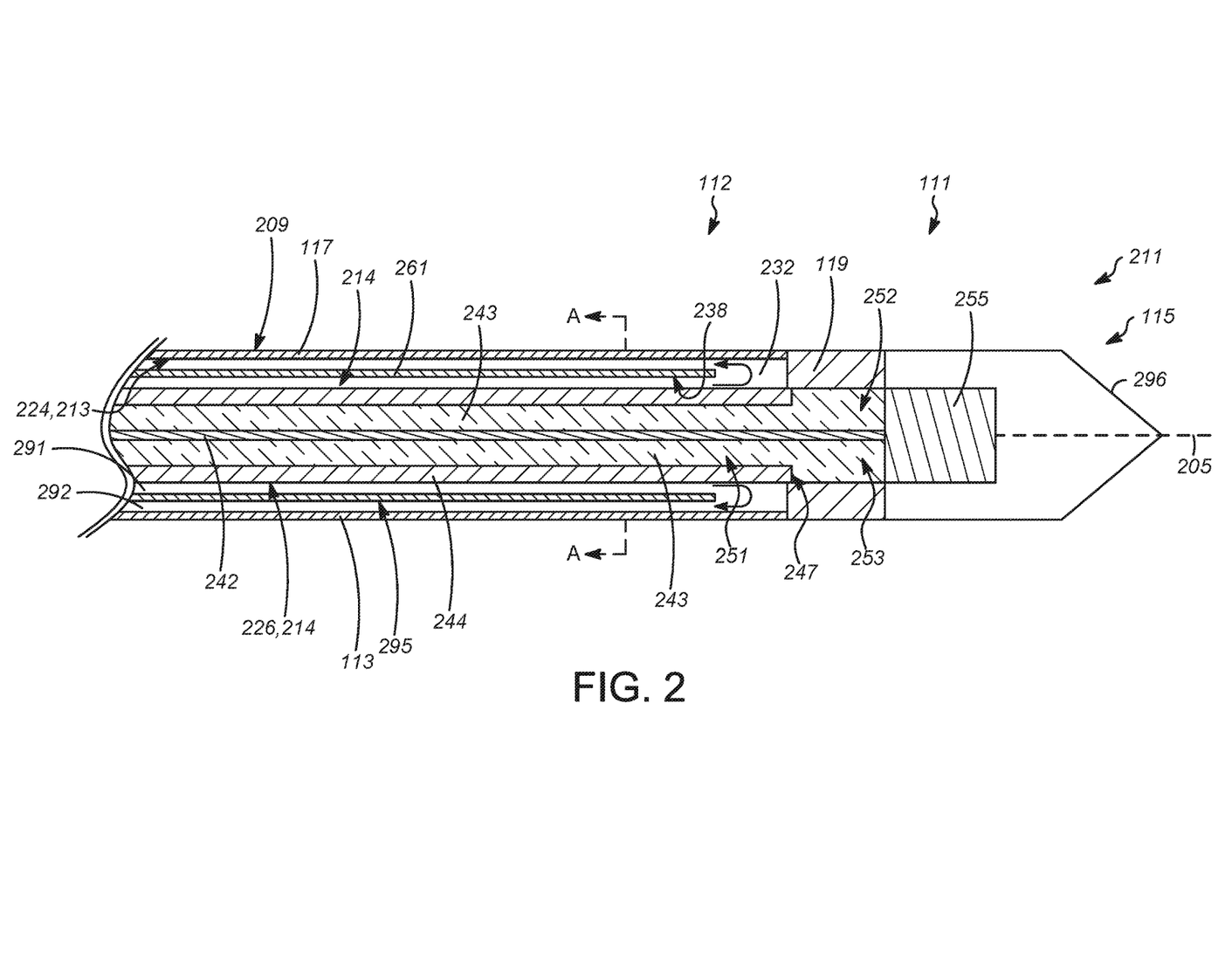
FIG. 2 is a cross-sectional view of a microwave ablation probe according to some examples.
Figure 3:
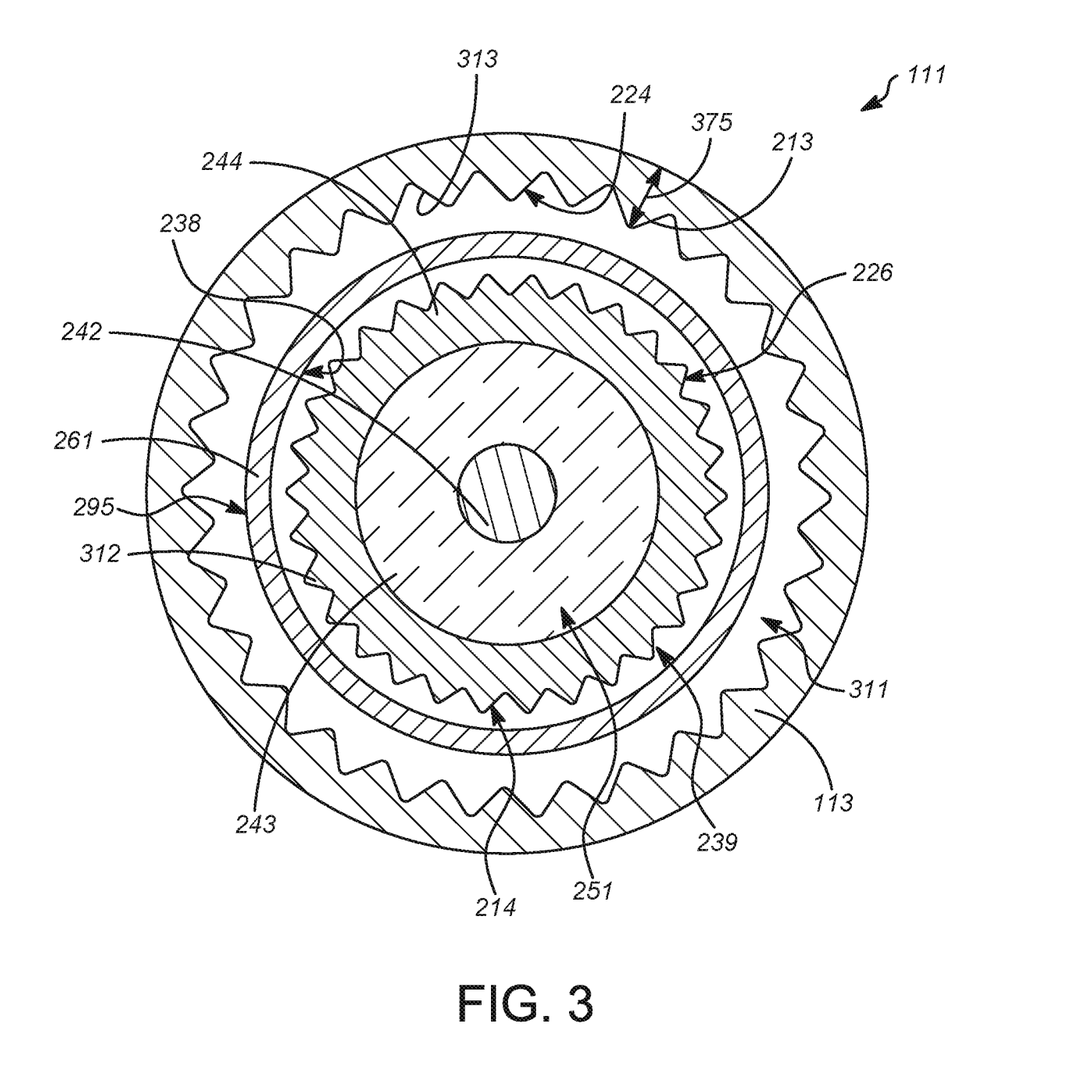
FIG. 3 is a cross-sectional view of a microwave ablation probe according to some examples.

FIG. 2 is a cross-sectional view of a microwave ablation probe that can be used in some examples of the disclosed technology. FIG. 3 is first example of a cross-section of the microwave ablation probe of FIG. 2 along line A-A. The ablation probe 111 includes a probe body 112 with a longitudinal axis 205. In some examples, the probe 111 includes a tissue-piercing distal tip 296. The cannula 113 includes a lumen 311. In some examples, the cannula 113 is a metal tube, such as a stainless steel hypodermic tube (hypotube). In alternative examples, the cannula 113 can be a polymer tube constructed of materials such as PEBA (polyether block amide), polyimide, polyether ether ketone (PEEK), or polytetrafluoroethylene (PTFE). In one example, the cannula 113 has an inner diameter of about 0.033 inch (0.84 mm), an outer diameter of about 0.039 inch (0.99 mm), and a wall thickness of about 0.003 inch (0.075 mm). In some examples, the outer diameter of the cannula 113 is at least about 18 gauge (1.02 millimeters), at least about 17 gauge (1.15 millimeters), or at least about 16 gauge (1.29 millimeters). In some examples, the outer diameter of the cannula 113 is at most about 12 gauge (2.01 millimeters), at most about 13 gauge (1.83 millimeters), or at most about 14 gauge (1.63 millimeters). It will be appreciated that other dimensions are possible for the cannula 113. The cannula 113 has an outer surface 209 and an inner surface 213. A cannula wall thickness 375 is defined between the outer surface 209 and the inner surface 213. The inner surface 213 forms a heat exchange surface 224 with surface features 313, which will be described in further detail below.

Adjacent to the shielded portion 117 is a radiation window 119, which is at least partially transparent to microwave energy. In some examples, the radiation window 119 is a tubular member that forms an extension of the surface of the probe body 112.

Coaxial Cable Antenna

Inside of the lumen 311 of the cannula 113 is the coaxial cable 251 that serves as a microwave ablation antenna 252. The coaxial cable 251 is connected to the microwave energy source 105. In some examples, the coaxial cable 251 is concentric with the cannula 113 and with the probe body 112. The coaxial cable 251 includes an inner conductor 242, an outer conductor 244, and an insulator 243 that is concentric with both the inner conductor 242 and the outer conductor 244. The insulator 243 electrically isolates the inner conductor 242 from the outer conductor 244. The insulator 243 can be a dielectric material such as a dielectric polymer. The outer conductor 244 has an outer surface 214 that serves as a heat exchange surface 226 with surface features 312, described in more detail below. The outer conductor 244 further has a distal boundary 247. The inner conductor 242 and the insulator 243 extend distally beyond the distal boundary 247 of the outer conductor 244. This portion of the coaxial cable 251 defines a radiating portion 253 at the distal portion 211 of the probe body 112. The radiating portion 253 extends distally beyond the distal boundary 247 of the outer conductor 244. The radiating portion 253 of the antenna 252 is configured to emit microwave energy that is transmitted from the microwave energy source 105 through the coaxial cable 251. The radiating portion 253 is aligned with the radiation window 119 so that microwave energy is transmitted from the antenna 252 into patient tissue when used for microwave ablation.

The coaxial cable 251 can have an outer diameter of at least about 0.5 millimeters, at least about 0.7 millimeters, at most about 2 millimeters, at most about 5 millimeters, ranging from about 0.5 to about 5 millimeters, or ranging from about 0.7 to about 2 millimeters. The coaxial cable 251 can be a coaxial cable having an outer diameter of about 0.864 millimeters, commercially available as part no. UT-034 from Micro-Coax, a Carlisle Interconnect Technologies Company, of Scottsdale, Ariz.

In the example of FIG. 2, the microwave antenna 252 is a dipole antenna. A conductive member 255 caps the distal end of the coaxial cable 251 at the insertion end 115 of the probe 111. In alternative examples (not shown), the microwave antenna 252 can be a monopole antenna, a slot antenna, or a triaxial antenna. In some examples, the probe 111 further includes a choke (not shown).

Irrigation Paths

In the example of FIG. 2, the probe 111 further comprises a liner 261. In some examples, the liner 261 is concentric with the cannula 113. The liner 261 has an inner surface 238 and an outer surface 295. The inner surface 238 defines a lumen 239. In some examples, the coaxial cable 251 is disposed inside the lumen 239 of the liner 261. In some examples, the coaxial cable 251 is concentric with the liner 261. In some examples, the liner 261 can be made of an insulating material such as a polymer tube or a fluoropolymer material. The liner 261 can be made of an electrically insulating material such as a polymer with a sufficiently high melt temperature to withstand heat created in the system. Some example materials include fluoropolymers or polyamide. A polyamide tubing can have a wall thickness of about 0.001 inch (0.025 mm), less than 0.001 inch (0.025 mm), at least about 0.001 inch (0.025 mm), or at least about 0.001 (0.025 mm) inch and at most about 0.002 inch (0.051 mm), with the wall thickness defined as the thickness between the inner surface 238 and the outer surface 295. A polymer tubing can have a wall thickness of about 0.003 inch (0.076 mm), at least about 0.003 inch (0.076 mm), or at least about 0.003 inch (0.076 mm) and at most about 0.004 inch (0.102 mm). In alternative examples, the liner 261 can be constructed from an insulated conductive material such as stainless steel tubing or Nitinol tubing with an insulating coating. The stainless steel or Nitinol tubing can have a wall thickness of at least about 0.002 inch (0.051 mm), between about 0.002 inch (0.051 mm) and about 0.004 inch (0.102 mm), between about 0.003 inch (0.076 mm) and about 0.004 inch (0.102 mm), or at most about 0.004 inch (0.102 mm).

In some examples, the inner diameter of the liner 261 is at least 0.001 inch (0.025 mm) greater than the outer diameter of the coaxial cable 251. In some examples, the inner diameter of the liner 261 is less than about 0.005 inch (0.127 mm) greater than the outer diameter of the coaxial cable 251. In some examples, the inner diameter of the cannula 113 is at least 0.001 inch (0.025 mm) greater than the outer diameter of the liner 261, and less than 0.005 inch (0.127 mm) greater than the outer diameter of the liner 261.

The probe body 112 defines an irrigation path 232 situated between the cannula 113 and the coaxial cable 251. The irrigation path 232 is configured to channel cooling fluid to and from the distal portion 211 of the probe body 112. The irrigation path 232 is defined by at least one wall or surface that comprises a heat exchange surface 224, 226. In some examples, the irrigation path 232 is divided into a first segment 291 and a second segment 292 by the liner 261 that is situated within the cannula 113. In the example of FIG. 2, the first segment 291 of the irrigation path 232 is defined between the outer surface 214 of the outer conductor 244 and the inner surface 238 of the liner 261. The second segment 292 is defined between the outer surface 295 of the liner 261 and the inner surface 213 of the cannula 113.

In some examples, the first segment 291 of the irrigation path 232 is an inlet path, and the second segment 292 of the irrigation path 232 is an outlet path. In such a case, the first segment 291 receives cooled fluid from the cooling source 135 through the first conduit 137, and the second segment 292 delivers circulated fluid from the distal portion 211 of the probe 111 out of the probe body 112 through the conduit 139. Cooling fluid conveyed through the first segment 291 is exposed to the outer conductor 244 of the coaxial cable 251, and cooling fluid conveyed through the second segment 292 is exposed to the inner surface 213 of the cannula 113.

In the example of FIG. 2, when the first segment 291 is an inflow path, cooling fluid entering the system is closer to the longitudinal axis 205 of the ablation probe 111 than the outflow path of the second segment 292. This allows the cooling fluid to flow into the probe body 112 to first encounter and cool the antenna 252 through contact with the heat exchange surface 226 on the outer surface 214 of the outer conductor 244, after which the cooling fluid travels around the distal end of the liner 261, now flowing toward a proximal end of the probe body 112, and exits the second segment 292, cooling the cannula 113 through contact with the heat exchange surface 224 on the inner surface 213 of the cannula 113. In alternative examples, the first segment 291 can be an outflow path and the second segment 292 can be an inflow path. In some examples, the heat exchange surfaces 224, 226 are coated with a wetting agent to increase the amount of heat conducted away from the surfaces 213, 214 by the cooling fluid.

In some examples, the flow rate of the cooling fluid through the irrigation path 232 can be between about 10 milliliter (ml) per minute and 90 ml per minute. In some examples, the flow rate can be between about 30 ml per minute and 50 ml per minute. The rate of coolant flow through the irrigation path 232 affects the heat transfer coefficient h. In some examples, the flow rate is at most about 40, 35, 30, 25, 20, 15, or 10 ml per minute.

In some examples, the temperature of the cooling fluid as it enters the system through the first conduit 137 is at the ambient temperature of the room. In some examples, the cooling fluid is below the ambient temperature of the room. In some examples, the temperature of the cooling fluid as it exits the system through the first conduit 137 is between about 0 and 20 degrees C. In some examples, the temperature of the cooling fluid increases by between about 1 and 10 degrees C. between when it enters the system through the first conduit 137 and exits the system through the second conduit 139.

In some examples, the cooling source 135 is configured to cool the fluid received through the conduit 139 and recirculate the fluid through the system. In alternative examples, coolant is not recirculated through the system. In some examples, a positive pressure forces fluid through the first conduit 137 into the probe body 112. In some examples, a negative pressure pulls fluid from out of the probe body 112 and through the second conduit 139 and back to the cooling fluid reservoir 135. In some examples, both positive pressure in the first conduit 137 and negative pressure in the second conduit 139 are provided.

Heat Exchange Surfaces

Figure 4:
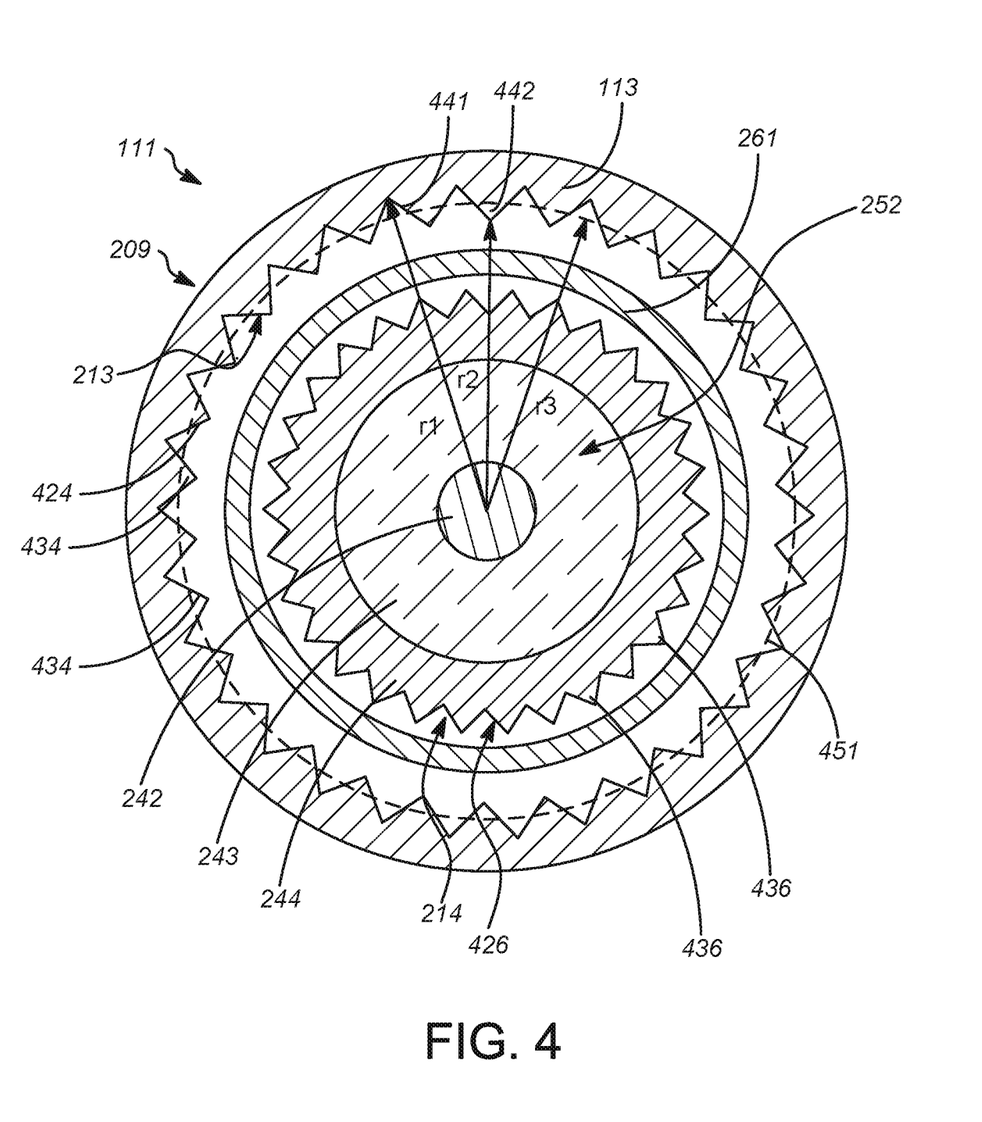
FIG. 4 is a cross-sectional view of an alternative example of a microwave ablation probe according to some examples.

The probe 111 can be provided with one or more heat exchange surfaces that increase the amount of heat that can be transferred out of the system by increasing the surface area that the cooling fluid comes in contact with. FIG. 4 is a second example of a cross-sectional view of the microwave ablation probe of FIG. 2 along the line A-A. In the example of FIG. 4, probe 111 includes cannula 113, antenna 252, and liner 261. The cannula 113 has an inner surface 213 and an outer surface 209. The inner surface 213 of the cannula 113 has a heat exchange surface 424 that comprises a plurality of convective fins 434 around the circumference of the inner surface 213. The convective fins 434 are axial corrugations. The antenna 252 has an inner conductor 242, an insulator 243, and an outer conductor 244. The outer conductor 244 has an outer surface 214 with a heat exchange surface 426 that comprises a plurality of convective fins 436. The convective fins 434 and 436 provide an increased area for the heat exchange surfaces 424 and 426 respectively versus a smooth, cylindrical surface lacking these convective fins. In the example of FIG. 4, the convective fins create peaks and troughs that have different distances from the longitudinal axis 205 of the probe 111. In this example, the convective fins extend axially along the inner surface 213 of the cannula 113 and the outer surface 214 of the outer conductor 244, parallel to the longitudinal axis 205. The surface features on the outer surface 214 of the outer conductor 244 and on the inner surface 213 of the cannula 113 can be manufactured using a number of different techniques, including mechanical, abrasive, laser, photoetching, chemical etching, machining, molding, extrusion, coldworking, or stretching techniques.

The heat exchange surfaces have surface features that can comprise corrugations, undulations, fins, one or more ridges, etc. In any of the examples described herein, the heat exchange surfaces can have a textured surface with peaks and troughs. The textured surface can increase the surface area along the irrigation path, allowing more cooling fluid to come into contact with the surface at any one time. In some examples, threading or knurling is used to create the texture. The knurled surface can include straight, angled, or crosshatched grooves. Alternatively, the surface can be dimpled or ribbed to increase the cooling surface area.

Heat exchange surfaces have a maximum radius, a minimum radius, and an average radius. For example, referring to heat exchange surface 424 in FIG. 4, a trough 441 has a distance $r_1$ that is a maximum radius from the longitudinal axis 205, and a peak 442 with a different distance $r_2$ that is a minimum radius from the longitudinal axis 205. The dashed line 451 represents the average distance $r_3$ of the heat exchange surface 424 from the longitudinal axis 205, where the average distance $r_3$ can be conceptualized qualitatively as being greater than the shortest distance $r_2$ from the longitudinal axis 205 to the heat exchange surface 424, but smaller than the farthest distance $r_1$ from the longitudinal axis 205 to the heat exchange surface 424. Effectively, this means that the inner surface 213 of the cannula 113 has a surface area greater than the surface area of a cylinder having a uniform radius $r_3$. Note that in the example of FIG. 4, the surface area of the heat exchange surface 424 is also greater than a cylinder having a uniform radius equal to $r_1$ or $r_2$. This increased surface area of the heat exchange surface 424 provides increased heat transfer between the cannula 113 and the cooling fluid versus a cannula with a smooth inner surface. The same effect is found with the heat exchange surface 426 having convective fins 436: the increased surface area of the heat exchange surface 426 allows heat to be transferred away from the antenna 252 at a greater rate compared to an antenna having a smooth outer surface.

Both the cannula 113 and the coaxial cable 251 are generally tubular. In some examples, the surface features of the heat exchange surfaces 224, 226 are implemented as an axial corrugation or ridge, extending parallel to the axis of the probe 111; a radial corrugation or ridge, extending circumferentially along the surface of the cannula 113 or coaxial cable 251; or a helical corrugation or ridge, extending helically around the surface of the cannula 113 or the coaxial cable 251.

The descriptions herein of the heat exchange surfaces 424, 426 of FIG. 4 generally are true of the heat exchange surfaces 224, 226 of FIG. 3, which also include convective fins which are axial corrugations. Compared to the convective fins 434, 436 of FIG. 4, the convective fins of the heat exchanges surfaces 224, 226 of FIG. 3 have rounded peaks and rounded troughs.

The probes of FIGS. 3 and 4 are shown with two heat exchange surfaces. In alternative examples, the probes of FIGS. 3 and 4 could be constructed with only one heat exchange surface. For example, the inner surface of the cannula could be a smooth surface with a uniform radius, and the heat exchange surface could be provided only on the outer surface of the outer conductor. Conversely, the outer surface of the outer conductor could be a smooth surface with a uniform radius, and the heat exchange surface could be provided only on the inner surface of the cannula.

Cannula Having Lumens

Figure 5:
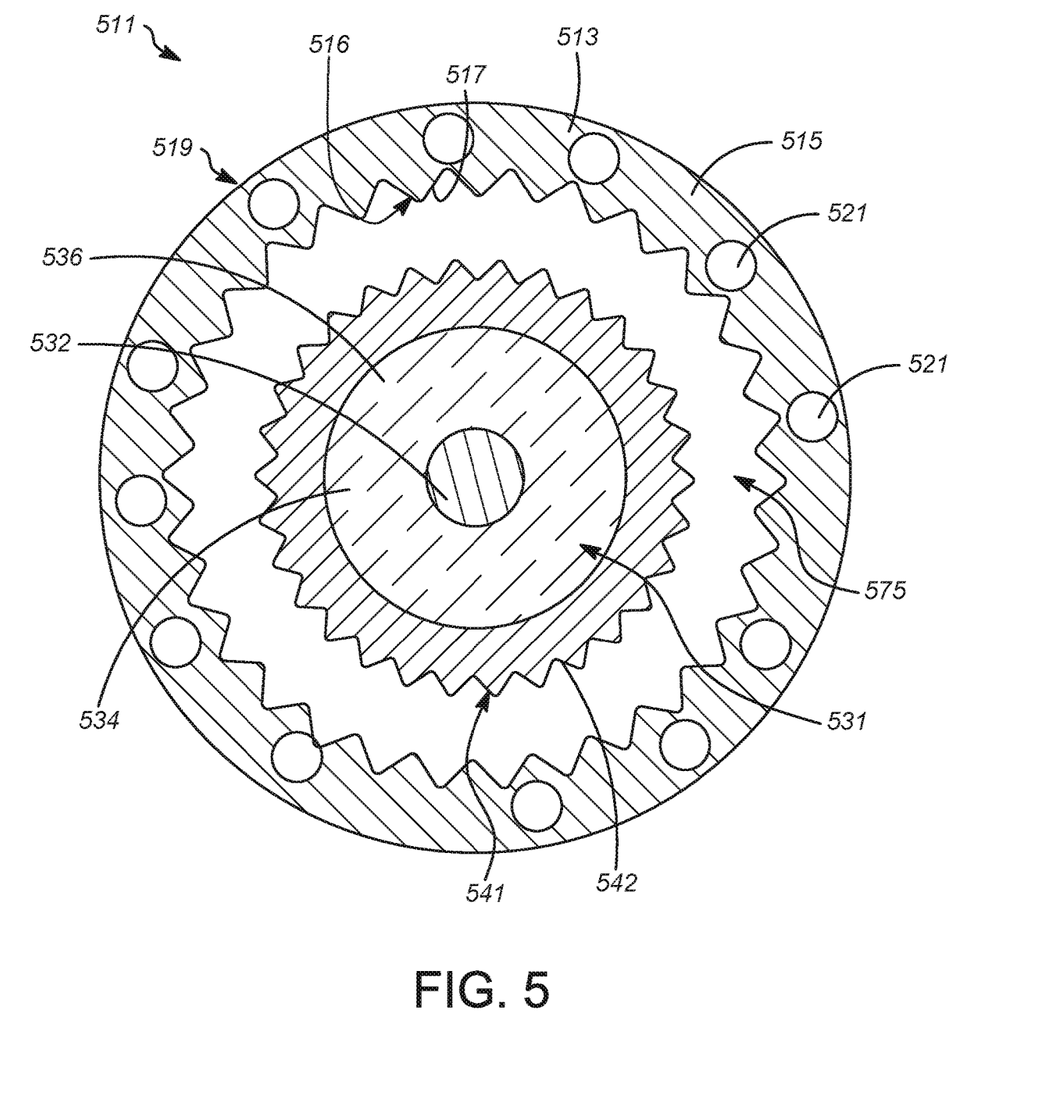
FIG. 5 is a cross-sectional view of an alternative example of a microwave ablation probe.

FIG. 5 is a cross-sectional view of an alternative example of a microwave ablation probe. In the example of FIG. 5, a probe 511 includes a cannula 513 with a cannula wall 515 that defines a plurality of lumens 521 running through the cannula wall 515. The lumens 521 are configured to channel cooling fluid to cool the probe 511. The inner surface 517 of the cannula 513 defines a lumen 575. Inside of the lumen 575 is a coaxial cable 531 that has an inner conductor 532, an outer conductor 534, and an insulator 536 separating the inner conductor 532 and the outer conductor 534. In some examples, the coaxial cable 531 is concentric with the cannula 513. The cannula 513 has a heat exchange surface 516 on an inner surface 517 of the cannula 513, and the coaxial cable 531 has a heat exchange surface 541 on an outer surface 542 of the outer conductor 534. The probe 511 is similar to the probe 111 in FIGS. 1-4, however, the probe 511 does not require a liner, because one portion of the irrigation path is defined by the lumens 521 in the cannula wall 515. Another portion of the irrigation path is defined by the lumen 575 between the inner surface 517 of the cannula 513 and the heat exchange surface 541 of the coaxial cable 531.

In some examples, the wall 515 of the cannula 513 is about 0.007 inch (0.178 mm) thick, and the lumens 521 span about 0.005 inch (0.127 mm) of the thickness of the wall 515, creating a thickness of about 0.001 inch (0.025 mm) between the lumens 521 and the outer surface 519 of the cannula 513.

In the drawing of FIG. 5, the probe 511 is shown with two heat exchange surfaces 516, 541. However, in alternative examples, the probe 511 could be constructed with only one heat exchange surface. For example, the inner surface 517 of the cannula 513 could be a smooth surface with a uniform radius, and the heat exchange surface 541 could be provided only on the outer surface 542 of the outer conductor 534. Conversely, the outer surface 542 of the outer conductor 534 could be a smooth surface with a uniform radius, and the heat exchange surface 516 could be provided only on the inner surface 517 of the cannula 513.

Helical Heat Exchange Surfaces

Figure 6:
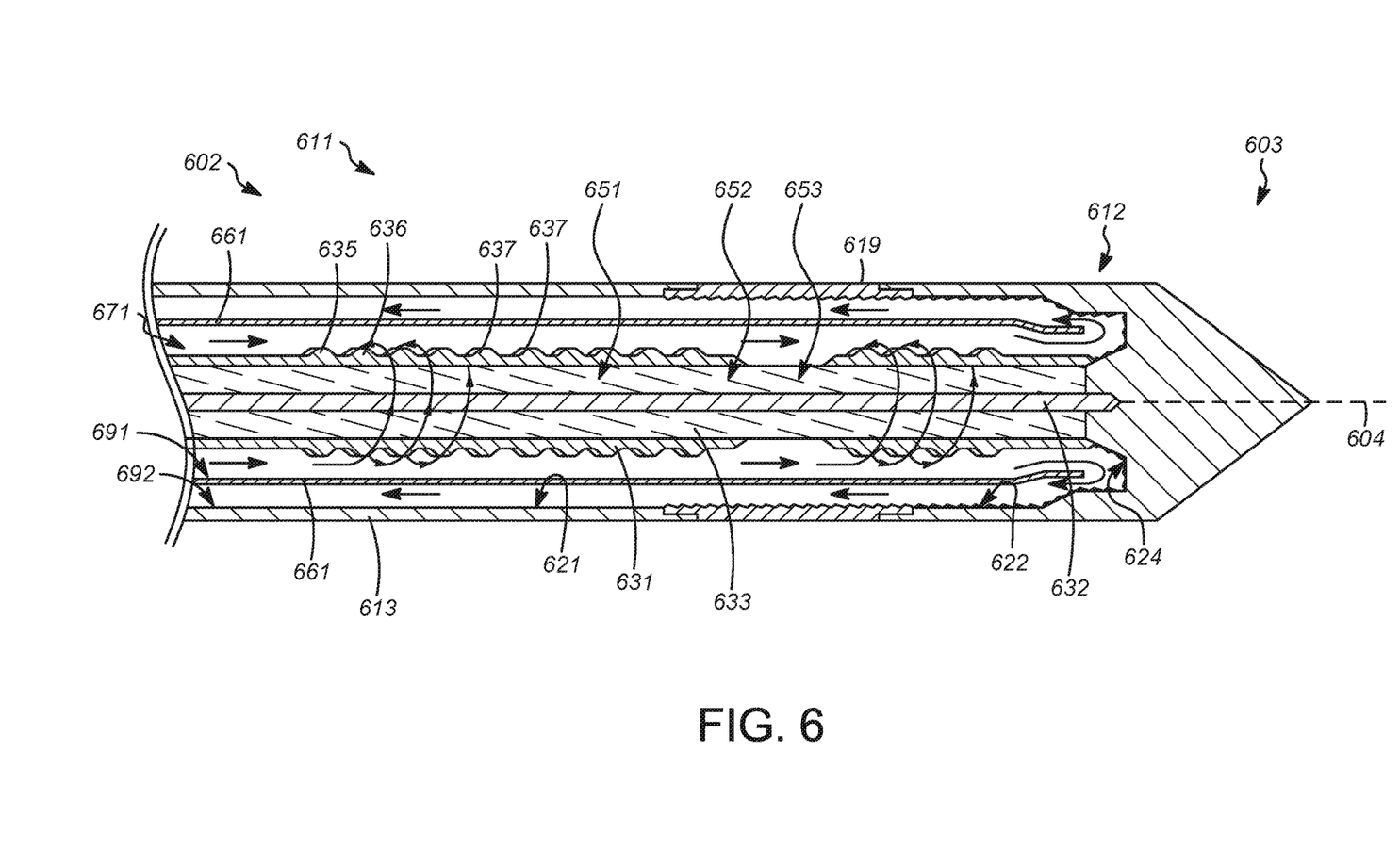
FIG. 6 is a cutaway cross-sectional view of an alternative example of a microwave ablation probe according to some examples.

In alternative examples of the disclosed technology, the geometry of the tubing causes the cooling fluid to follow a nonlinear path through the body of the ablation probe. FIG. 6 is a cutaway cross-sectional view of an alternative example of a microwave ablation probe according to some examples. The probe 611 includes a cannula 613, a coaxial cable 651, and a liner 661. In the example of FIG. 6, the cannula 613, the liner 661, and the coaxial cable 651 are concentric around a longitudinal axis 604 of the probe 611. The probe body 612 has a proximal portion 602 and a distal portion 603. The coaxial cable 651 has an inner conductor 632, an outer conductor 631, and an insulator 633 that electrically isolates the inner conductor 632 and the outer conductor 631. An antenna 652 includes a radiating portion 653 that is aligned with a radiation window 619 of the probe body 612.

The outer conductor 631 has a heat exchange surface 636 with a plurality of ridges 637 on the outer surface 635 of the outer conductor 631. The ridges 637 give the outer conductor 631 a non-uniform thickness. In the example of FIG. 6, the ridges 637 wrap around the exterior of the coaxial cable 651 helically, similar to a threaded screw. The ridges 637 define peaks and troughs that vary in distance from the longitudinal axis 604 of the probe body 612. The ridges 637 of the heat exchange surface 636 direct cooling fluid to flow helically around the outer surface 635 of the outer conductor 631. In some examples, the ridges 637 comprise alternating peaks and troughs. In some examples, the outer conductor 631 has a minimum wall thickness of about 0.001 inch (0.025 mm). In some examples, the peaks of the ridges 637 increase the wall thickness of the outer conductor 631 by about 0.001 inch (0.025 mm). In some examples, the distance between adjacent ridges 637 is between about 0.001 inch (0.025 mm) and 0.005 inch (0.127 mm). In some examples, the peaks of the ridges 637 have a flattened shape. In alternative configurations, the peaks of the ridges 637 can have other shapes, such as rounded, triangular, etc.

Similarly, the cannula 613 has an inner surface 621 that defines a heat exchange surface 622. The heat exchange surface 622 has surface features that include a plurality of undulations 624 on the inner surface 621 of the cannula 613. The undulations 624 define peaks and troughs that vary in distance from the longitudinal axis 604 of the probe body 612, creating an increased surface area.

An irrigation path 671 is defined between the cannula 613 and the coaxial cable 651. The irrigation path 671 can be separated into a first segment 691 and a second segment 692. The first segment 691 can be defined between the heat exchange surface 636 of the outer conductor 631 and the liner 661, and the second segment 692 can be defined between the heat exchange surface 622 of the cannula 613 and the liner 661. In some examples, the first segment 691 is an inflow path for coolant to enter the probe body 612, and the second segment 692 is an outflow path for coolant to exit the probe body 612.

The helical configuration of the ridges 637 of the heat exchange surface 636 directs coolant entering the first segment 691 into a helical path around the outer circumference of the coaxial cable 651. Coolant that follows a helical path in the probe body 612 spends more time in contact with the heat exchange surface 636 than if the coolant were flowing in a direction parallel to the longitudinal axis 604 of the probe 611. The more time the coolant can spend in contact with the heat exchange surface 636, the more heat the coolant can absorb and transfer away from the probe body 612.

In some examples, the ridges 624 create a fluid dynamic in which there is a high pressure drop across the irrigation path 671 between the first segment 691 and the second segment 692. This causes an increased flow velocity of the coolant along the helical path created by the ridges 624.

In the drawing of FIG. 6, the probe 611 is shown with two heat exchange surfaces 622, 636. However, in alternative examples, the probe 611 could be constructed with only one heat exchange surface. For example, the inner surface 621 of the cannula 613 could be a smooth surface with a uniform radius, and the heat exchange surface 636 could be provided only on the outer surface 635 of the outer conductor 631. Conversely, the outer surface 635 of the outer conductor 631 could be a smooth surface with a uniform radius, and the heat exchange surface 622 could be provided only on the inner surface 621 of the cannula 613.

Wetting Agents for Heat Exchange Surfaces

In any of the foregoing examples, any of the heat exchange surfaces can be coated with a wetting agent to improve contact between the heat exchange surface and the cooling fluid, improving heat transfer. Additionally, in some cases the polarity of the heat exchange surface can repel molecules of the cooling fluid of a different polarity. A wetting agent can correct the polarity of the cooling fluid at the surface of the electrode to correct for this effect. Wetting agents can also correct surface effects created by textured surface elements on the heat exchange surface. For example, some wetting agents can prevent unwanted gas bubbles from forming on the surface of the heat exchange surface. Some examples of wetting agents that can be appropriate are sodium stearate, sodium lauroyl sarcosinate (INCI), perfluorononanoate, perfluorooctanoate (PFOA or PFO), alkylbenzene sulfonates lignin sulfonates, fatty alcohol ethoxylates, and alkylphenol ethoxylates. Fluorosurfactants, siloxane surfactant, polypropylene oxides, and many other classes of wetting agents can alternatively be used.

Cap Construction

The cap can be constructed from a metal such as brass or stainless steel. In some examples, the cap can be constructed from a ceramic material. In some examples, the cap has a sharp trocar tip with sufficient structural integrity to pierce tissue, allowing the ablation probe to be inserted into the tissue to be ablated. If the cap is made from a metal material, the metal length can be varied to provide the variable length for the antenna. If the cap is made from a ceramic material, the cap length will not affect the resonant frequency of the antenna.

Microwave Ablation Methods

During ablation treatment, a physician can adjust a number of parameters in the microwave ablation system to create the desired ablation lesion. The parameters can alternatively be automatically adjusted by a controller in a computer system. The amount of power provided to a microwave energy source can be adjusted. A higher or lower amount of power to be delivered either increases or decreases the intensity of the microwave radiation entering the tissue. Ablation at high power can effectively create a large lesion. If the power is too high, negative effects can occur, such as tissue charring. The system can also adjust the amount of time that the microwave radiation is delivered to the tissue. A shorter time period is associated with less risk for charred tissue, however, if the ablation treatment is terminated too early, the treatment may not successfully ablate all of the tissue that is desired to be ablated.

The microwave ablation system of the current disclosure can be used to perform a method of treatment. The method can be used with a system including a probe having a probe body with a shielded portion and a radiation window that is at least partially transparent to microwave energy. The shielded portion comprises a cannula. The probe further includes a coaxial cable within the probe body. An antenna in the probe is electrically connected with the cable. The antenna has a radiating portion for emission of microwave energy, and the radiating portion is aligned with the radiation window.

The probe body also defines an irrigation path configured to carry cooling fluid to and from the distal portion of the probe body. At least one wall defining the irrigation path has a heat exchange surface. The heat exchange surface has an average radius, and the surface area of the heat exchange surface is larger than a surface area of a smooth surface with a radius equal to the average radius.

The method includes delivering cooling fluid to the irrigation path, circulating the cooling fluid within the probe body, and delivering microwave energy to the antenna via the cable. The method can also include returning the cooling fluid back to the cooling fluid source after it returns from the distal end of the probe body, It should be noted that, as used in this specification and the appended claims, the singular forms include the plural unless the context clearly dictates otherwise. It should also be noted that the term "or" is generally employed in its sense including "and/or" unless the content clearly dictates otherwise. It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications referenced in this specification are herein incorporated by reference in their entirety.

The disclosed technology has been described with reference to various specific and preferred embodiments and techniques. However, it should be understood that many variations and modifications may be made while remaining within the spirit and scope of the technology.

The invention claimed is:

1. A microwave ablation probe comprising:
a probe body comprising a shielded portion and a radiation window that is at least partially transparent to microwave energy, wherein the shielded portion comprises a cannula;
a liner concentric with and within the cannula, wherein the liner is formed from an insulating material,
a coaxial cable within the probe body; and
an antenna comprising a radiating portion for emission of microwave energy at a distal portion of the probe body, wherein the radiating portion is aligned with the radiation window;
a probe tip disposed at a distal end of the probe body;
wherein the probe body defines an irrigation path configured to carry cooling fluid to and from the distal portion of the probe body, wherein a first segment of the irrigation path is defined between the outer surface of the outer conductor and an inner surface of liner, wherein a second segment of the irrigation path is defined between an outer surface of the liner and an inner surface of the cannula, wherein a distal end of the irrigation path terminates proximally to the probe tip;
wherein at least one wall defining the irrigation path comprises a heat exchange surface, wherein the heat exchange surface comprises one or more convective fins extending axially along the heat exchange surface and parallel to a longitudinal axis of the probe body;
wherein the convective fins are defined along at least a portion of an inner surface of the cannula and at least a portion of an outer surface of an outer conductor of the coaxial cable; and
wherein the heat exchange surface has an average radius, wherein a surface area of the heat exchange surface is larger than a surface area of a smooth surface with a radius equal to the average radius.

2. The probe of claim 1 wherein the heat exchange surface comprises corrugations, undulations, fins, one or more ridges, an axial corrugation, a helical corrugation, a radial corrugation, a helical ridge, a radial ridge, or an axial ridge.

3. The probe of claim 1 wherein the heat exchange surface varies in distance from a longitudinal axis of the probe.

4. The probe of claim 1 wherein the heat exchange surface is located on at least a portion of the outer surface of the outer conductor of the cable.

5. The probe of claim 1 wherein the heat exchange surface is located on at least a portion of the inner surface of the cannula.

6. The probe of claim 1 wherein the heat exchange surface comprises a helical ridge on at least a portion of the outer surface of the outer conductor of the coaxial cable.

7. The probe of claim 1 wherein the heat exchange surface comprises a helical ridge on at least a portion of an inner surface of the cannula.

8. The probe of claim 1 wherein the heat exchange surface comprises a helical ridge on at least a portion of the outer surface of the outer conductor of the coaxial cable, wherein the probe further comprises an additional heat exchange surface, the additional heat exchange surface comprising a helical ridge on at least a portion of an inner surface of the cannula.

9. The probe of claim 1 further comprising a coolant source configured to deliver the cooling fluid to the irrigation path and receive the cooling fluid.

10. The probe of claim 1 wherein the first segment of the irrigation path is an inlet path and the second segment of the irrigation path is an outlet path.

11. The probe of claim 1 wherein the cannula comprises a cannula wall that defines at least one lumen for a flow of cooling fluid.

12. The probe of claim 1, wherein at least a portion of the heat exchange surfaces is coated with a wetting agent configured to improve contact between the heat exchange surface and the cooling fluid.

13. The probe of claim 1, wherein the cannula comprises a cannula, the cannula wall defining a plurality of lumens running through the cannula wall and parallel to the longitudinal axis of the probe body, wherein the plurality of lumens defines a portion of the irrigation path.

14. The probe of claim 1, the liner comprising an electrically insulating material.

15. The probe of claim 1, the liner comprising an insulated conductive material.

16. The probe of claim 1, wherein an inner diameter of the liner is less than about 0.127 mm greater than an outer diameter of the coaxial cable.

17. A microwave ablation system comprising a microwave energy source, a cooling fluid source, and a microwave ablation probe, the probe comprising:
a probe body comprising a shielded portion and a radiation window that is at least partially transparent to microwave energy, wherein the shielded portion comprises a cannula; and
a coaxial cable within the probe body connected to the microwave energy source, the coaxial cable comprising a center conductor, a dielectric material surrounding the center conductor, and an outer conductor having an outer surface and a distal boundary, wherein the center conductor comprises a radiating portion that extends beyond the distal boundary of the outer conductor, wherein the radiating portion is configured for emission of microwave energy, wherein the radiating portion is aligned with the radiation window;

a probe tip disposed at a distal end of the probe body;

wherein the probe body defines an irrigation path configured to carry cooling fluid to and from a distal portion of the probe body, wherein the cooling fluid source is in fluid communication with the irrigation path, wherein a distal end of the irrigation path terminates proximally to the probe tip;

wherein at least one wall defining the irrigation path comprises a heat exchange surface, wherein the heat exchange surface comprises one or more convective fins extending axially along the heat exchange surface and parallel to a longitudinal axis of the probe body;

wherein the heat exchange surface has an average radius, wherein a surface area of the heat exchange surface is larger than a surface area of a smooth surface with a radius equal to the average radius; and wherein the cannula comprises a cannula wall, the cannula wall defining a plurality of lumens running through the cannula wall and parallel to the longitudinal axis of the probe body, wherein the plurality of lumens defines a portion of the irrigation path.

18. The probe of claim 17 further wherein the convective fins are defined along at least a portion of an inner surface of the cannula and at least a portion of an outer surface of an outer conductor of the coaxial cable.

19. A microwave ablation method comprising:
providing a microwave ablation probe comprising:
a probe body comprising a shielded portion and a radiation window that is at least partially transparent to microwave energy, wherein the shielded portion comprises a cannula,
a liner concentric with and within the cannula, wherein the liner is formed from an insulating material,
a coaxial cable within the probe body, and
an antenna electrically connected with the coaxial cable and within the probe body, the antenna having a radiating portion for emission of microwave energy at a distal portion of the probe body,
a probe tip disposed at a distal end of the probe body;
wherein the radiating portion is aligned with the radiation window, wherein the probe body defines an irrigation path configured to carry cooling fluid to and from the distal portion of the probe body, wherein a first segment of the irrigation path is defined between the outer surface of the outer conductor and an inner surface of liner, wherein a second segment of the irrigation path is defined between an outer surface of the liner and an inner surface of the cannula wherein a distal end of the irrigation path terminates proximally to the probe tip;
wherein at least one wall defining the irrigation path comprises a heat exchange surface, wherein the heat exchange surface comprises one or more convective fins extending axially along the heat exchange surface and parallel to a longitudinal axis of the probe body, wherein the heat exchange surface has an average radius, and wherein a surface area of the heat exchange surface is larger than a surface area of a smooth surface with a radius equal to the average radius, wherein at least a portion of the heat exchange surfaces is coated with a wetting agent configured to improve contact between the heat exchange surface and the cooling fluid; and
delivering cooling fluid to the irrigation path; and
delivering microwave energy to the antenna via the coaxial cable.

20. The method of claim 19 further comprising receiving cooling fluid back from the irrigation path at a cooling fluid source.

* * * * *